United States Patent [19]
Thomas

[11] Patent Number: 5,181,824
[45] Date of Patent: Jan. 26, 1993

[54] VARIABLE WIDTH AND LENGTH HOLDING AND SIZE SEBSUBG DEVICE FOR A DUAL AXIS TRANSLATION MECHANISM

[75] Inventor: Howard C. Thomas, Westminister, Colo.

[73] Assignee: Eureka Acquisition Corp., Arlington Heights, Ill.

[21] Appl. No.: 616,478

[22] Filed: Nov. 21, 1990

[51] Int. Cl.$^5$ .............................. B65G 35/00
[52] U.S. Cl. ....................... 414/751; 378/176; 294/119.1
[58] Field of Search ............... 414/749–753; 294/119.1, 67.33; 378/172, 176; 269/71, 73

[56] References Cited

U.S. PATENT DOCUMENTS

| | | | |
|---|---|---|---|
| 3,355,730 | 11/1967 | Neasham | 340/286 |
| 3,383,506 | 5/1968 | Bock et al. | 250/66 |
| 3,555,276 | 1/1971 | Endesfelder et al. | 250/58 |
| 3,848,134 | 11/1974 | Gieschen et al. | 250/471 |
| 4,005,782 | 2/1977 | Crockett | 414/753 X |
| 4,071,767 | 1/1978 | Pury et al. | 250/444 |
| 4,105,920 | 8/1978 | Pury et al. | 250/402 |
| 4,327,596 | 5/1982 | Simon | 414/749 X |
| 4,357,538 | 11/1982 | Hunt et al. | 378/175 |
| 4,412,383 | 11/1983 | Landa | 33/1 M |
| 4,417,357 | 11/1983 | Le Sonn | 378/177 |
| 4,420,886 | 12/1983 | Amano | 33/1 M |
| 4,489,428 | 12/1984 | Schwieker | 378/181 |
| 4,559,641 | 12/1985 | Caugant et al. | 378/181 |
| 4,577,341 | 3/1986 | Schwieker et al. | 378/150 |
| 4,819,978 | 4/1989 | Scheinman et al. | 294/119.1 |
| 4,845,734 | 7/1989 | Maki et al. | 378/181 |
| 5,010,564 | 4/1991 | Thomas | 378/176 |

FOREIGN PATENT DOCUMENTS 1948037 3/1975 Fed. Rep. of Germany.
323655 8/1957 Switzerland.

Primary Examiner—David A. Bucci
Assistant Examiner—Donald W. Underwood
Attorney, Agent, or Firm—Lawrence C. Edelman

[57] ABSTRACT

A dual axis translation mechanism for holding and moving an object of variable dimension to a position defined by first and second axis. The mechanism includes a frame, a carriage mounted on the frame for movement with respect to the frame in the first axis, and an object holding means coupled with the carriage for holding and moving the object with respect to the carriage in the second axis. A motor selectively drives a first shaft and a drive/brake assembly provides a second shaft which, in a drive mode of the assembly is driven synchronously with the first shaft and, which in a brake mode of the assembly is held non-driven while the first shaft is being driven. First and second endless belts are mounted for rotating movement within the frame and extend in a direction parallel to the first axis. The first and second belts are coupled to the first and second shafts, respectively, for receiving selective rotational movement therefrom, with the first belt also being coupled to the object holding means for causing selective movement of the object in a direction parallel to the second axis and the second belt being coupled with the carriage for causing selective movement of the carriage in a direction parallel to the first axis. The object holding means comprises as lead-screw having an end coupled to receive rotational movement in response to rotation of the first belt, and carries first and second nuts thereon, which are coupled to the first and second clamp arms, respectively.

33 Claims, 6 Drawing Sheets

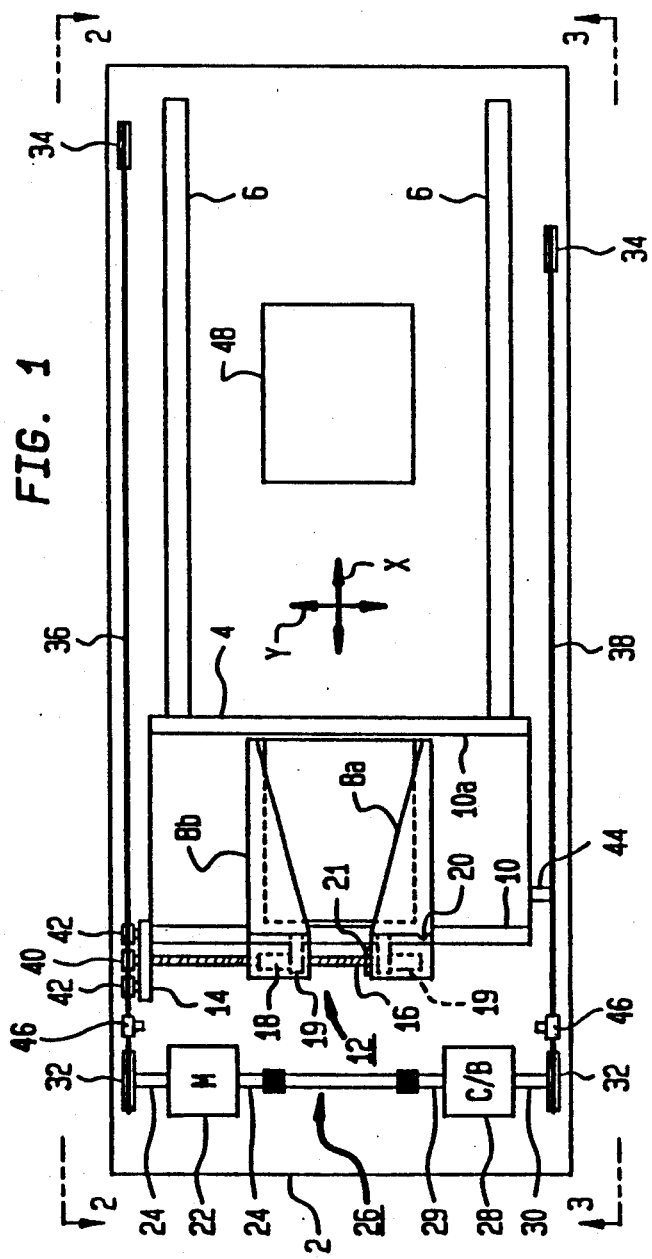
FIG. 1
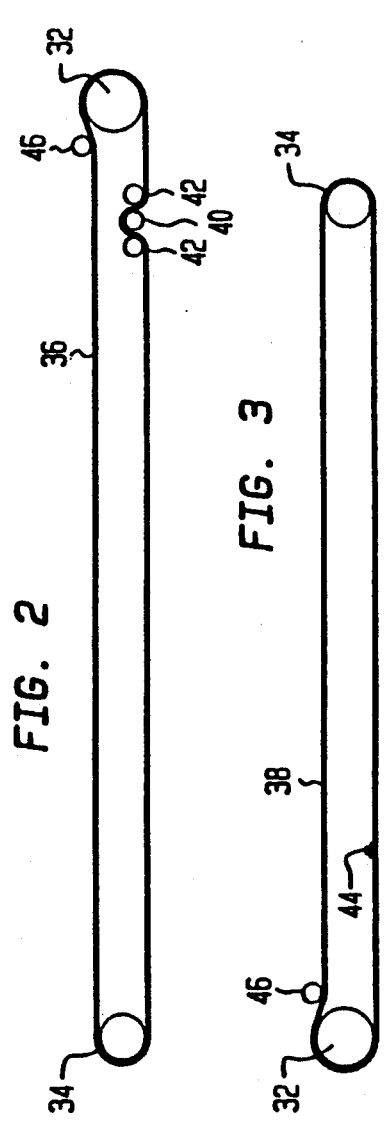
FIG. 2
FIG. 3
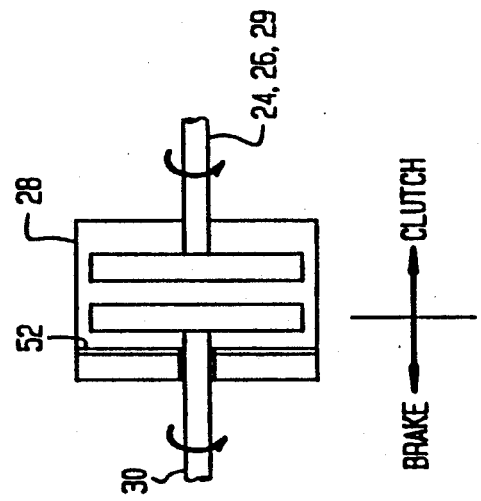
FIG. 4

VARIABLE WIDTH AND LENGTH HOLDING AND SIZE SEBSUBG DEVICE FOR A DUAL AXIS TRANSLATION MECHANISM

CROSS-REFERENCE TO RELATED APPLICATION

This application is related to an application which is assigned to the same assignee as the present application and was filed on Sept. 14, 1989, U.S. Ser. No. 07/406,991, entitled DUAL AXIS TRANSLATION MECHANISM.

BACKGROUND OF THE INVENTION

1. Field of the Invention

This invention relates generally to a holding device for a dual axis translation mechanism and in particular to an x,y translation mechanism useful in an x-ray spot film device which can accept film cassettes of varying width and length.

2. Description of the Prior Art

Conventional spot film devices usually comprise a support or frame extending crosswise over the top of an x-ray table. A main carriage is mounted on the support for being advanced from a rearward parked position to a frontward radiographic position wherein a film cassette carried by an inner carriage is disposed in alignment with an x-ray beam that is projected through a patient from a collimated x-ray source in the table. The film cassette is mounted or held in a tray supported on the inner carriage which is translatable with respect to the main carriage so that the center of the collimated x-ray beam may be made coincident with a selected area on the film cassette where one or a sequence of spot film exposures are to be made. The area is further defined by a superimposable x-ray mask. Due to differences in the size of the image to be made and the number of areas to be used on the film, different size films and film cassettes are available for use in the spot film devices.

As is well known, spot film devices are also used in conjunction with a fluoroscopic device which permits an examining radiologist to visualize anatomy of interest before making one or more radiographs in a choice of sizes by translating the film cassette forward and shifting it, and the mask, to obtain the desired sequence of radiographs. The fluoroscopic device on the spot film device is aligned with the x-ray source in the table, and the film cassette is, of course, retracted from the x-ray beam during fluoroscopy.

When a fluoroscopic view of interest is observed, the film cassette must be positioned into the x-ray beam path rapidly and one or more exposures must be taken while the fluoroscopically observed condition persists.

The x,y translating mechanism of spot film devices generally employs multiple electromechanical means for receiving varying sizes of film cassettes and rapidly advancing and retracting the film cassette between load and parked positions and between parked and the various positions in which the sequence of radiographs are taken. In addition, means are provided for predetermining the sequence and for cushioning the shock forces that are incidental to rapid transfer of the film cassette carriage from the parked position to its other positions when alternating between fluoroscopic and radiographic or loading modes. Furthermore, the spot film device must have some way of sensing the size of the inserted film cassette in order to properly control its above-noted movements.

These functions have been achieved in known translation mechanisms by complicated arrangements of mechanical linkages, multiple motors, tracks, cams, relays, belts and so forth, which accomplished their purposes under manual or mechanical influence or under a combination of such influences. Cassette translation mechanisms including motor drive means typically include two reversible motors, one motor for each of the orthogonal directions in which the film cassette must be driven. Additionally, one or two smaller motors are typically used in order to control grasping of differently sized film cassettes. The requirement of two or more motors undesirably increases the weight and power consumption of the drive system. In other types of motor drive systems having one and/or two motors, as a motor moves the film cassette rearwardly to a parked or home position, it slowly loads a return spring at the same time. The film carriage is latched in the parked position and when the latch is released, the carriage is advanced rapidly under the influence of the spring and halted abruptly in the radiographic position. Rapid movement and abrupt halt of the film carriage results in considerable noise, shock and vibration that necessitates use of shock absorbing devices such as dash pots to reduce these ill effects. One problem with this type of system is that the main carriage must be returned to a rearward position after each exposure, to reload the spring, after which the carriage must be projected forwardly again to make the next exposure.

Other types of prior spot film devices have a set of tracks for the main carriage. After each exposure, the carriage is returned rearwardly and shifted to different tracks, similar to railroad car switching. When the carriage is driven forwardly, it arrives in the proper position for the next exposure to be made. This is a relatively slow method and requires a large and complicated mechanism which has many moving parts.

Prior art cassette holding and size sensing mechanisms typically comprise motors or spring driven sliding and/or pivoting clamp arms for holding and engaging the film cassette and include potentiometers and/or encoders connected to the clamp arms for providing size sensing information signals.

The above complex arrangements have resulted in lower than desirable reliability and serviceability, increased power consumption, a massiveness that has had to be off-set with increased counterweight and/or power and a noisy operation. Some of the complexity and size resulted from spot devices being adapted to accommodate rectangular rectangular cassettes in both their long and short dimensions in which case means had to be provided for altering the mode of operation of the transfer and sequence mechanism depending on how the cassette was oriented in its holder.

My prior U.S. Pat. No. 5,010,564 entitled DUAL AXIS TRANSLATION MECHANISM relates to a translation mechanism particularly useful in a spot film device that is simple in construction, lightweight, operates quietly, efficiency, safely, and automatically, is simple to operate and maintain and is comparatively inexpensive to manufacture. More specifically, my above-noted patent discloses a mechanism for selective translation of an object, such as a film cassette, along first and second axes, comprising a frame, a carriage mounted on the frame for movement with respect to the frame along a first axis, an object holder for holding said object and an intermediate mounting means coupled to the object holder and the carriage for mounting the object holder on the carriage for movement with respect to the carriage along a second axis which is different from the first axis. A motor is provided for selectively driving a first shaft. A drive/brake assembly provides a second shaft which, in a drive mode of the assembly is caused to be driven synchronously with the first shaft and, which in a brake mode of the assembly, is held non-driven while the first shaft is being driven. First and second endless belts are mounted for rotating movement within the frame and extend along the first and second shafts, respective, for selectively receiving rotational movement therefrom. The first belt is also coupled to the intermediate mounting means so as to drive a portion thereof for causing selective movement of the object holder along the second axis and the second belt is coupled with the carriage for causing selective movement of said carriage along the first axis. In operation, when both belts are synchronously rotated, the second belt causes the carriage to move along the first axis, while the intermediate mounting means does not cause movement of the object holder because of the synchronous movement of the intermediate mounting means with respect to the first belt, due to the coupling of the intermediate mounting means on the carriage. However, when the second belt is not driven during the brake mode of the drive/brake assembly, relative movement of said first belt with respect to said intermediate mounting means causes movement of the object holder along the second axis.

Controlled movement of the first and second shafts by the motor and drive/brake assembly results in the ability to rapidly position the object holder at any desired position along the first and second axes in a simple, efficient and reliable manner.

In a preferred embodiment, the drive/brake assembly comprises a clutch/brake assembly having an input shaft which is driven by the same motor which drives the first shaft.

The present invention is directed to incorporating a holder for variable size objects as well as an object size sensing mechanism into my above-described dual axis translation mechanism.

SUMMARY OF THE INVENTION

A dual axis translation mechanism of the type noted above, wherein the intermediate mounting means comprises a lead-screw having an end coupled to receive rotational movement in response to rotation of said first belt. The lead-screw carries first and second nuts thereon, which are coupled to first and second clamp arms, respectively. The clamp arms are used for selectively grasping and thereafter positioning differently sized objects. The first nut is threaded onto said lead-screw and attached to said first clamp arm in a manner which does not allow said first nut to rotate, while said second nut is attached to said second clamp arm in a manner which allows said second nut to at least selectively rotate with respect to said second clamp arm. In a preferred embodiment, said second nut is threaded onto said lead screw and a nut clamping mechanism causes said second nut to be selectively clamped to said second arm so as to not allow rotational movement of said second nut with respect to said second clamp arm when said nut is clamped and when said nut is unclamped, allows said second nut to spin freely with respect to said second clamp arm. Initially, said second nut is unclamped and said second arm is held in place. Rotation of said lead-screw causes said first clamp arm to be driven towards said second clamp arm so as to firmly grasp any object inserted therebetween. Thereafter, said second nut is clamped, so that said first and second arms thereafter move in unison, with said grasped object therebetween, in response to further rotation of said lead-screw.

Other features and advantages of the invention will be apparent from the description of the preferred embodiment of the invention and from the claims.

For a fuller understanding of the present invention, reference should now be made to the following detailed description of the preferred embodiment of the invention and to the accompanying drawings.

BRIEF DESCRIPTION OF THE DRAWINGS

FIG. 1 illustrates in a simplified manner a top view of a dual axis translating mechanism including an object holder constructed in accordance with the principles of the invention;

FIGS. 2 and 3 illustrate by a side view details of the first and second drive belts illustrated in FIG. 1;

FIG. 4 illustrates in simplified form the clutch/brake assembly shown in FIG. 1;

DETAILED DESCRIPTION OF THE PREFERRED EMBODIMENTS

FIG. 1 shows a top view of the mechanical portions of the dual axis translating mechanism, arranged for use in a spot film device. The electrical portions of the arrangement are not shown since they are of conventional design for a spot film device, with some slight variations (e.g., for controlling the clutch/brake mechanism, to be described) which would be obvious to those of ordinary skill in the art. A frame 2 includes a carriage 4 which is mounted within the frame for sliding movement along a first axis, indicated by arrow X, via guide means 6. Guide means 6 preferably comprises a set of parallel-spaced ball-bearing linear slides, in order to allow smooth rapid movement of carriage 4 along the x-axis.

Figure 8:
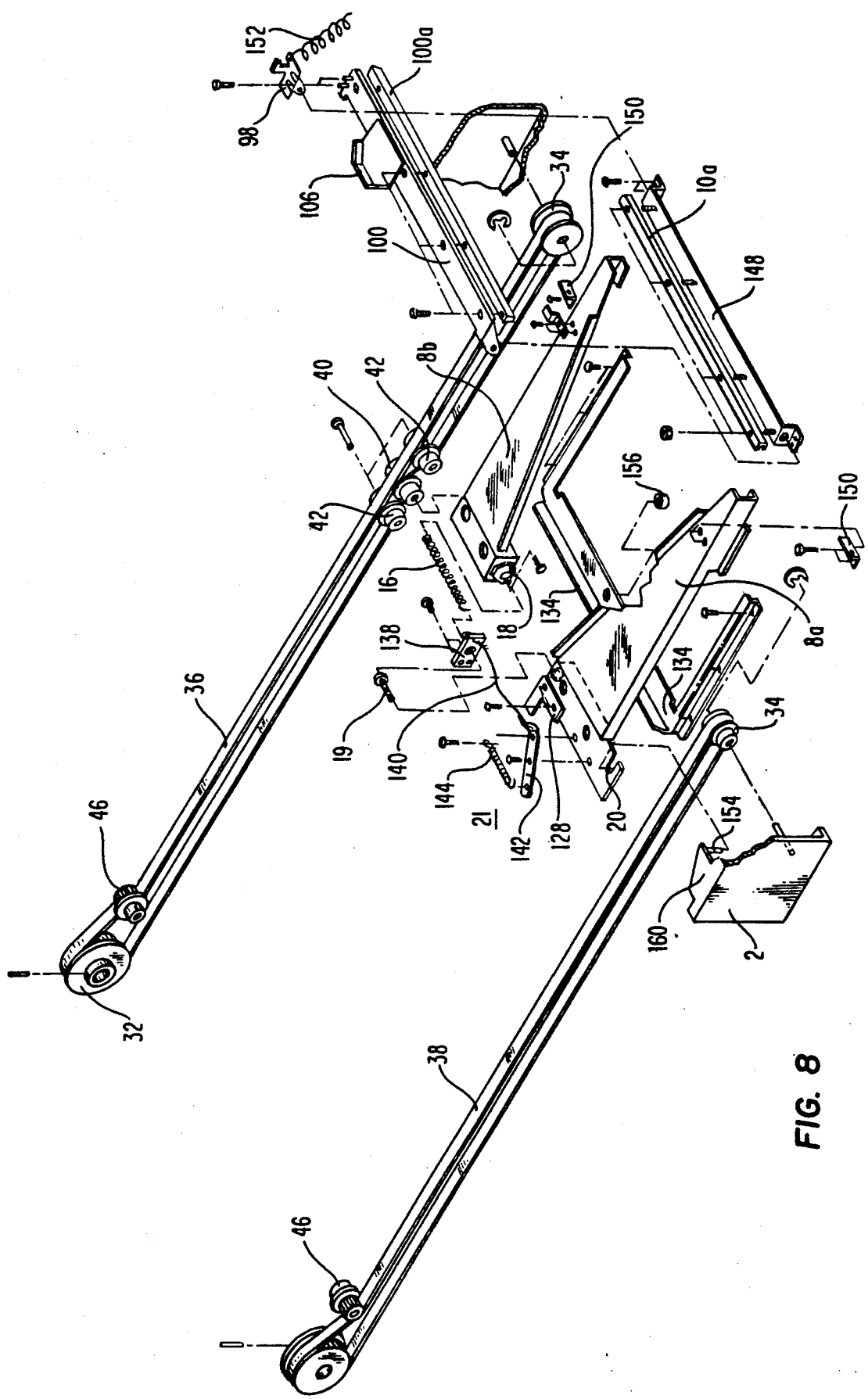

An object holder 8 including clamp arms 8a and 8b is mounted on carriage 4 for sliding movement along a second axis, indicated by arrow Y, via an intermediate mounting means including parallel-spaced guide means 10 and 10a, as well as a lead-screw assembly 12. Guide means 10 comprises a ball-bearing linear slide and guide means 10a comprises a nylon bar, for slidingly supporting the tips of object holder 8. Lead-screw assembly 12 is mounted to carriage 4 via a bracket 14 and includes a rotatable lead-screw 16 having a following nut 18 which is non-rotatably coupled to clamp arm 8b. Rotation of lead-screw 16 causes linear movement of nut 18, and thus object holder 8, in the y-axis direction. Lead-screw 16 also includes a following nut 19 which, unlike following nut 18, is coupled to clamp arm 8a in a manner which allows nut 19 to be at least selectively rotatable with respect to clamp arm 8a (as will be described in greater detail later on). Additionally, clamp arm 8a has an extending tab portion including a slot 20 which engages a pin extending from a portion of frame 2, for locking clamp arm 8a in the "wide-open" position when carriage 4 is moved forward and to its rightmost position along the x-axis (hereinafter called the LOAD position). A nut clamping means 21, shown in greater detail in FIG. 8, is also provided on clamp arm 8a for unclamping nut 19 from arm 8a so as to allow rotational movement between nut 19 and clamp arm 8a when carriage 4 is in the LOAD position. In this manner, when object holder 8 is in the LOAD position, clamp arms 8a and 8b are spaced apart by their maximum amount, but when a film cassette is inserted between the arms and lead-screw 16 is caused to turn, clamp arm 8b is driven toward clamp arm 8a until it firmly grips the loaded film cassette. Immediately upon rearward movement of carriage 4, nut 19 of clamp arm 8a becomes clamped to arm 8a so as to prevent its rotation, causing clamp arms 8a and 8b to thereafter move in unison in accordance with the rotational movement of lead screw 16. This structure and operation will be described in greater detail later on.

A motor 22 is provided for selectively driving a first shaft 24. One end of shaft 24 is coupled, via a flexible coupling 26, to a clutch/brake assembly 28 for selectively driving a second shaft 29, 30. As well known, when assembly 28 is in its clutch mode of operation, its drive shafts 29 and 30 rotate synchronously, while in its brake mode of operation, drive shaft 29 (and hence shaft 24) is allowed to rotate while shaft 30 is held so as to not rotate. Details of clutch/brake assembly 28 are shown in FIG. 4 and described later on. Shafts 24 and 30 each include a drive pulley 32 at their ends and frame 2 includes corresponding idler pulleys 34 for supporting first and second endless belts 36 and 38, respectively, so that the belts extend within frame 2 along the x-axis direction. Belt 36 is coupled to lead-screw assembly 12 via pressure of belt 36 against a drive pulley 40 attached to one end of lead-screw 20. The pressure is exerted via idler pulleys 42 which are rotatably attached to bracket 14. Belt 38 is connected to carriage 4 via a clamp type of connecting means 44.

FIGS. 2 and 3 show right and left side views of the above-described details of the connection of belts 36 and 38, respectively, and additionally show the use of further idler pulleys 46 mounted within frame 2 for maintaining proper tension in belts 36 and 38. When the above-described arrangement is used in a spot film device for holding a film cassette and controlling its position, frame 2 would include a port 48 therein through which the x-rays which pass through the patient are allowed to impinge upon the film grasped by object holder 8.

The basic x,y translation operation of the above-described arrangement is as follows. For movement of object holder 8 in the x-axis direction, motor 22 is energized for rotation of shaft 24 in the desired direction for an appropriate time period while clutch/brake assembly 28 is caused to be in its clutch mode. As shafts 24, 29 and 30 rotate, belts 36 and 38 rotate at the same speed, with belt 38 causing movement of carriage 4 in the x-axis direction. Since lead-screw assembly 12 is mounted upon carriage 4, it also moves in the x-axis direction, thereby resulting in no relative movement between lead-screw assembly 12 and belt 36. Thus, when clutch/brake assembly 28 is in the clutch mode, appropriate energization of motor 22 controls the speed and sense of movement of object holder 8 in the x-axis direction. However, when clutch/brake assembly 28 is in the brake mode, shaft 30 is held non-rotating, while shafts 29, 24 rotate. Thus, belt 38 is held non-rotating, preventing movement of carriage 4, while belt 36 is rotated, thereby driving pulley 40 of lead-screw assembly 12 and causing movement of object holder 8 in the y-axis direction. Consequently, appropriate energization of motor 22 and clutch/brake assembly 28 allows complete control for positioning object holder 8 anywhere within the x-y coordinate axis system.

FIG. 4 illustrates in simplified form, details of the clutch/brake assembly 28 shown in FIG. 1. The opposing ends of shafts 30 and 24, 26 are enlarged and coated with a suitable material (or include an appropriate apparatus therebetween) so that when shaft 30 is urged to the right (as shown in FIG. 4) by an electromechanical shifting means (not shown) of known design, both shafts will be coupled so as to rotate in synchronism, resulting in the clutch mode of operation of assembly 28. However, when shaft 30 is urged to the left, its enlarged end is forced into contact with an abrasive material 52, resulting in rapid deceleration and non-rotation of shaft 30, while shafts 24, 29 are allowed to continue to rotate, resulting in the brake mode of operation.

Figure 5:
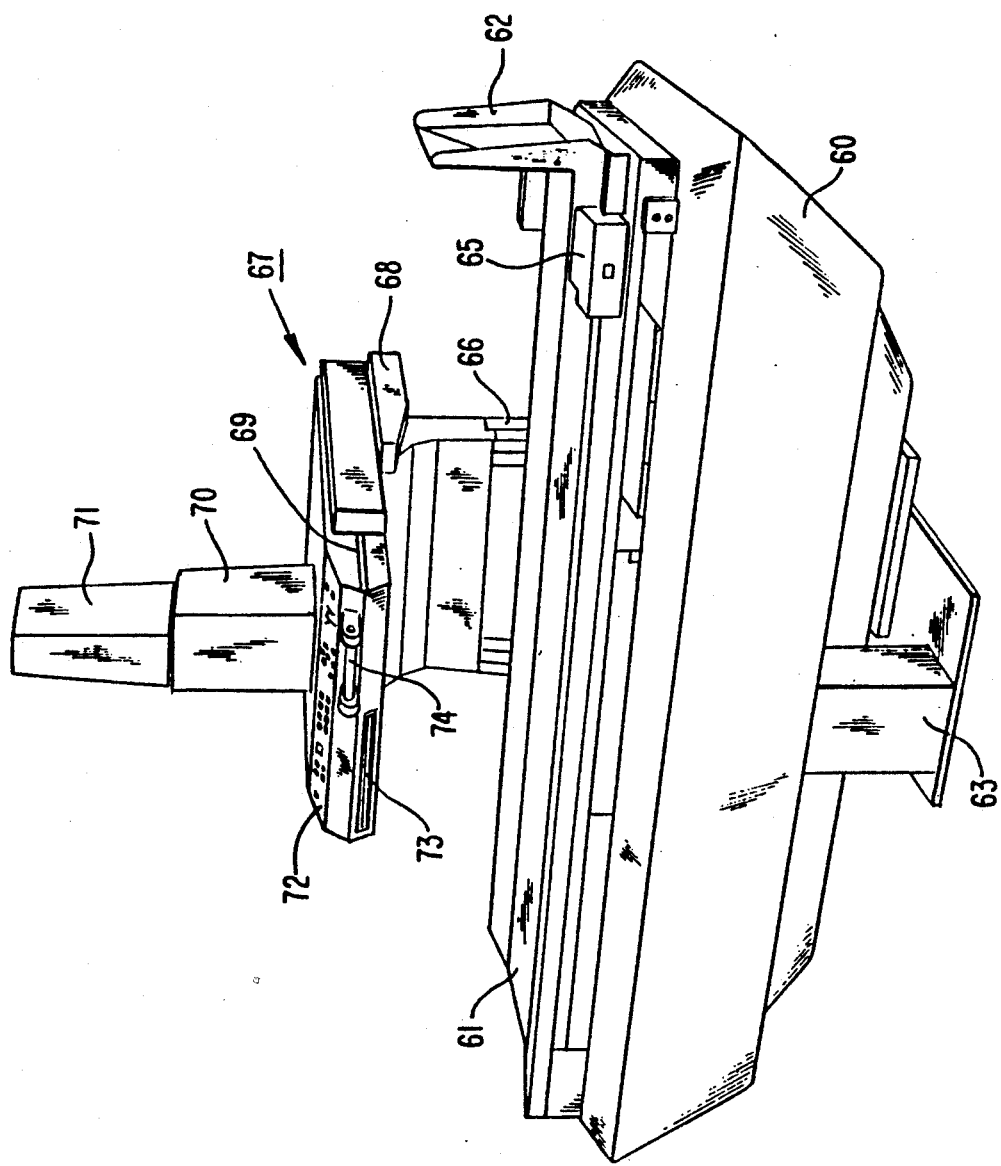
FIG. 5 illustrates a diagnostic x-ray table including a spot film device.

FIG. 5 is a perspective view of a typical diagnostic x-ray table incorporating a spot film device improved in accordance with the present invention. The table comprises a body 60 in which there is an x-ray source, not shown. When energized, the x-ray source projects a collimated x-ray beam through table top 61 on which a patient undergoing x-ray examination may be reposed. The top has a foot rest 62 for supporting the patient in an upright position when the table body 60 is tilted clockwise from the position in which it is shown. Table body 60 is supported from a floor stand 63 with respect to which body 60 may be tilted and translated to clear the floor with a mechanism and driving means of conventional design (not shown). A locking mechanism 65 holds foot rest 62 to table top 61 in any desired position along the tables length.

The x-ray source is mounted on a carriage which is not visible but is located within table body 60 and is adapted for being translated in opposite directions lengthwise of the patient. Extending upwardly from the carriage at the rear of the table is a column 66 which may be extended and contracted in a direction orthogonal to table top 61.

The improved spot film device is generally designated by reference numeral 67. It is supported on column 66 by means of a bearing support 68 that cooperates with a pair of bearing rails, such as the one marked 69, to enable the spot film device to be shifted manually to a limited extent crosswise of the table top forward to a locked examining position and locked toward a rear parked position.

Mounted to the top of spot film device 67 and near its front is a fluoroscopic device 70 including an x-ray image intensifier. A television camera, not shown, mounted within a housing 71 is used to display the x-ray image obtained during a fluoroscopic procedure on a television monitor, which is not shown but is well known to those who are skilled in the art.

A control panel 72 for operating the spot film device is located at its front end. Spot film device 67 has a front opening 73 for inserting and withdrawing a film cassette at the front of the table and a power assist handle 74 for controlling the position of the spot film device.

FIGS. 6, 7, 8 and 9 illustrate details of the mechanical arrangement of the spot film device shown in FIG. 5. The reference numerals used in the preceding figures will be used herein for similarly functioning corresponding elements.

Figure 6:
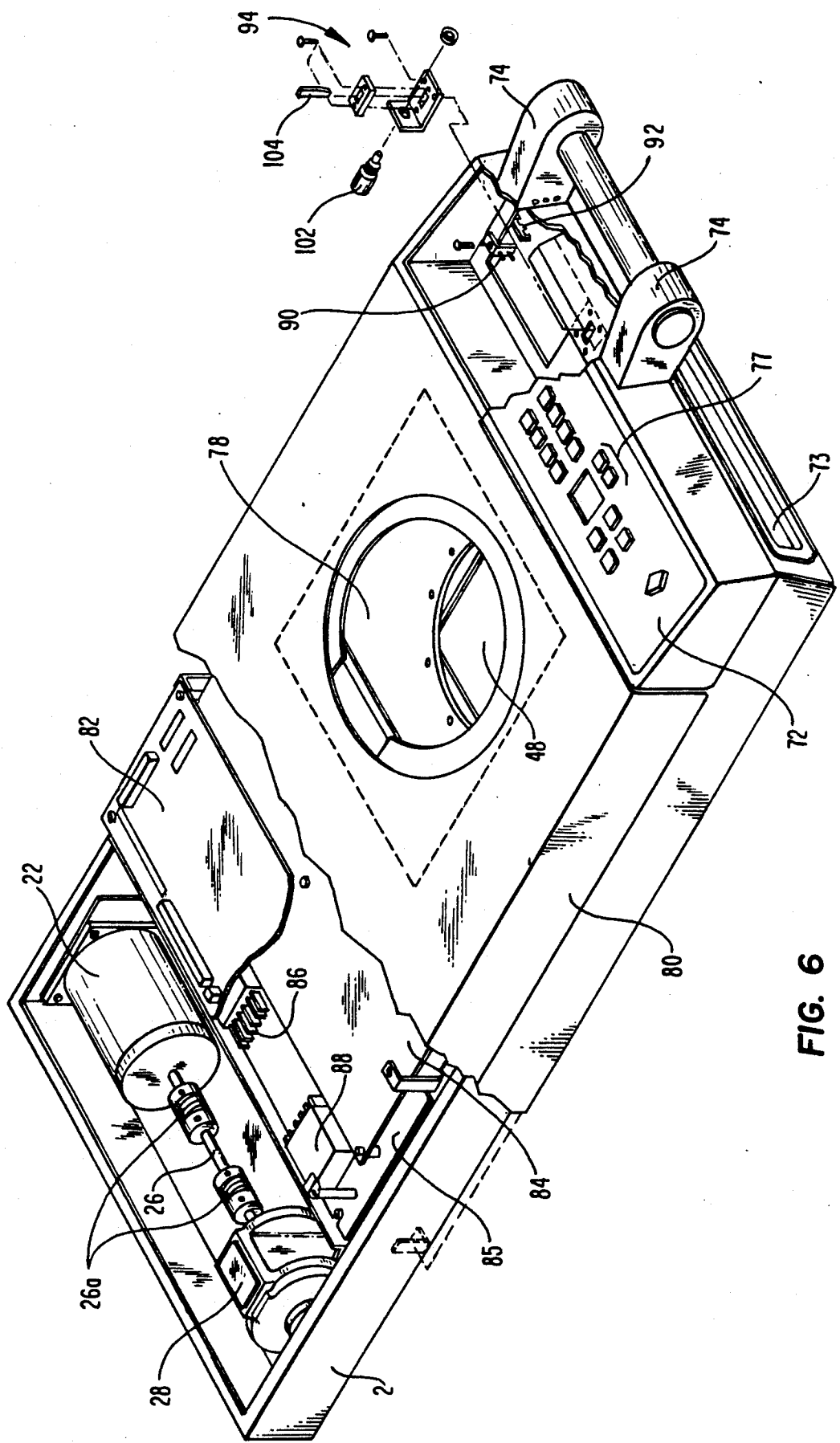
FIGS. 6, 7, 8 and 9 illustrate construction details of an x-ray spot film device having a multi-sized film cassette holder and translation mechanism constructed in accordance with the principles of the present invention.

In FIG. 6 the details of control panel 72 are shown as including a plurality of push-buttons for format selection, collimator control, table top position, table tilting, etc. A display 76 is also provided which comprises an array of LED's for displaying a graphic illustration of the format selection. Directly underneath display 76 is a two digit display 77 for indicating the size of the film cassette inserted into the spot film device. X-ray port 48 is lead lined and includes a mounting arrangement 78 aligned therewith for the attachment of fluoroscopic device 70 above spot film device 67. In the rearward portion of spot film device 67, the cover 80 is shown cut-away so as to reveal the interior thereof. Thus, the position of motor 22 is shown as well as couplings 26a for coupling shaft 24 to clutch/brake assembly 28. Also shown are a circuit board 82 for mounting the relay/interface circuitry, a circuit board 84 mounted on a supporting platform 85 for the computer control circuitry (not specifically shown) and isolated and non-isolated power supplies 86 and 88, respectively. Motor 22 is a conventional four lead, four phase, 1.8° stepper motor driven by a 80 VDC, 6 amp, 20 kHz microstepping bi-polar chopper drive. Clutch/brake 28 is model CB-170 available from various well known electrical parts manufacturers, e.g., Electroid Corporation, etc.

A portion of control panel 72 is shown cut-away so as to reveal optical sensors 90, 92 and a solenoid arrangement 94. Sensor 90 interacts with a flag 96 (shown in FIG. 8) mounted on arm 8b to indicate when arm 8b is in the LOAD position. Sensor 92 interacts with a flag 98 mounted on a cassette latch 100 (also shown in FIG. 8) to indicate that carriage 4 has moved to the LOAD position and also to indicate if cassette retaining latch 100 is opened or closed. Solenoid arrangement 94 includes a solenoid 102 mounted in frame 2 and including a plunger for selectively activating a lever 104 which (as shown in FIG. 8) pushes on a tab 106 protruding from cassette retaining latch 100, for tilting latch 100 backwards and thereby releasing a film cassette out of holder 8 via opening 73 of the spot film device.

Figure 7:
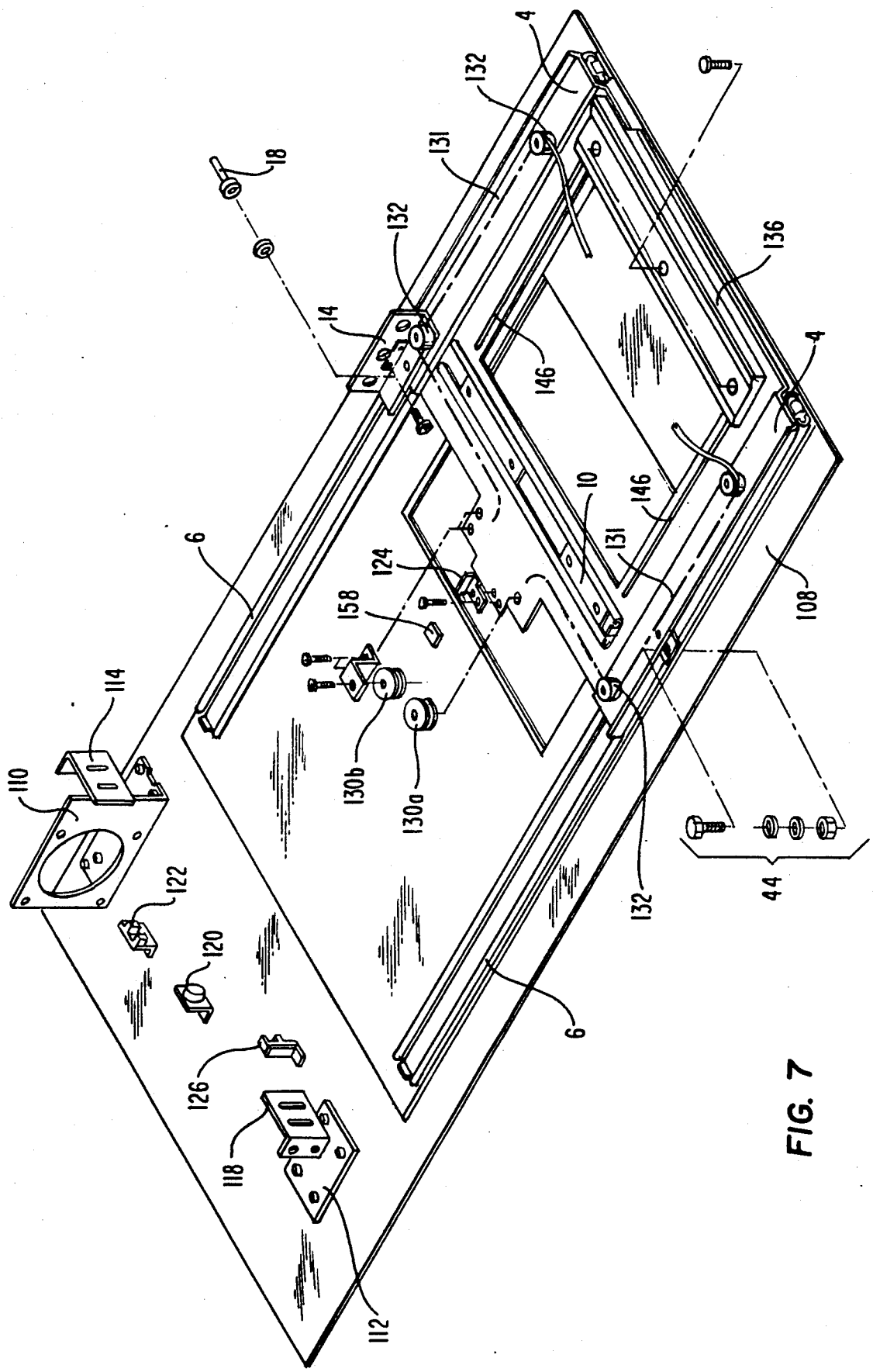

FIG. 7 illustrates additional details relating to the mounting of components within frame 2. Thus, the bottom 108 of frame 2 is shown, upon which mounting brackets 110 and 112 are provided for mounting motor 22 and clutch/brake assembly 28, respectively in their operating position. Additionally, brackets 114 and 116 are mounted on studs (mounted on the upper part of frame 2, not shown) for locating adjustable idler pulleys 46 (shown in FIGS. 2, 3 and 8). An outside edge of carriage 4 includes a tab portion 118 having a hole therein for receiving pin arrangement 44 for clamping belt 38 to carriage 4. A rubber bumper 120 is provided to stop carriage 4 during its rearward motion towards the HOME position (rear left corner of frame 2), an optical sensor 122 is used, in conjunction with a flag 124 mounted on a rear edge of carriage 4, to sense when carriage 4 has been driven to the rear of frame 2, and a sensor 126 is used in conjunction with a flag 128 mounted on a rear portion of arm 8a (as shown in FIG. 8), to sense when holder 8 has returned to the HOME position. Constant force (1-3 lbs.) reel springs 130a and 130b are mounted on a rear portion of carriage 4, each reel spring being coupled to a cable 131 (shown in dashed lines) which runs along the periphery of carriage 4 and around pulleys 132 to a draw bar 134 (shown in FIG. 8). Draw bar 134 receives and supports the leading edge of the inserted film cassette and provides a constant forward tension thereon which is useful for urging the film cassette against a lip 100a of latch 100 and for ejecting the film cassette at the proper time. A front portion of carriage 4 includes a riser 136 for supporting the trailing edge of the inserted film cassette so as to elevate and suspend it in a level position until its edges firmly are grasped by clamp arms 8a and 8b.

FIG. 8 illustrates details of object holder 8 adapted to grasp, position, and thereafter release the film cassette. Lead-screw 16 passes through a rear portion of clamp arm 8b which includes following nut 18 mounted therein in a non-rotating manner for causing linear movement of clamp arm 8b in accordance with rotational movement of lead-screw 16. Lead-screw 16 also passes through a rear portion of clamp arm 8a, which includes following nut 19 rotatably mounted therein, and a clamp mechanism 21 which selectively urges a shoulder of following nut 19 against clamp arm 8a so as to prevent rotational movement of nut 19 with respect to clamp arm 8a. Clamp mechanism 21 includes a clamp plate 138 secured at one end to clamp arm 8a and at its other end urged towards clamp arm 8a via a cable 140, lever 142 and spring 144. Draw bar 134 is mounted on slides 146 (shown in FIG. 7) which are mounted on carriage 4, and is urged into a forward position by the tension created by reel springs 130a, b and cable 131 (also shown in FIG. 7).

Returning again to FIG. 8, cassette latch 100, including a film cassette retaining lip 100a, is pivotally mounted on a bracket 148 which in turn is mounted on carriage 4. Nylon slide 10a is also shown, mounted on bracket 148, and includes a rearward facing slot for engaging pins 150 mounted near the tips of each of clamp arms 8a, b, so as to support the tip portions of clamp arms 8a, b as previously noted. The right end of cassette latch 100 is mounted to bracket 14B in a pivoting manner using the bottom of flag 98, which flag, as previously noted, also cooperates with sensor 92 (shown and described with respect to FIG. 6) to indicate that a film cassette has been properly latched and furthermore when the carriage is in the LOAD position. A spring 152 connected between flag 98 and carriage 4 urges latch 100 into a normally closed position.

Also shown in FIG. 8 is tab 106 mounted upon cassette latch 100 which tab has a raised rearward edge which interacts with solenoid actuated lever 104 (shown and described with respect to FIG. 6) for selectively tilting cassette latch 100 back for ejection of a film cassette. It is noted that upon insertion of a film cassette, latch 100 is forced to tilt upward due to the leading edge of the film cassette pushing upon the beveled outside edges of latch 100. Then draw bar 134 is pushed rearward until the film cassette is fully inserted and spring 152 closes latch 100. This action also loads reel springs 130a, b and holds the film cassette in place until ejection. When latch 100 is tilted back by operation of solenoid 102 for ejection, reel springs 130a, b cause draw bar 134 to eject the film cassette out through opening 73. FIG. 8 also shows in more detail retaining slot 20, located on the outside edge of clamp arm 8a, which cooperates with a pin 154 of frame 2 for holding clamp arm 8a in the "wide-open" position when carriage 4 is in the LOAD position. Draw bar 134 also includes a magnet 156 mounted in the bottom center portion thereof which cooperates with a hall-effect sensor 158 mounted on the floor of frame 2 (shown in FIG. 7) which is used to determine the length of the inserted film cassette, as will be described later on. Flag 96 is also shown mounted near the tip of clamp arm 8b, which as previously described with respect to FIG. 6, cooperates with sensor 90 to indicate when clamp arm 8a is also in the LOAD position.

Figure 9:
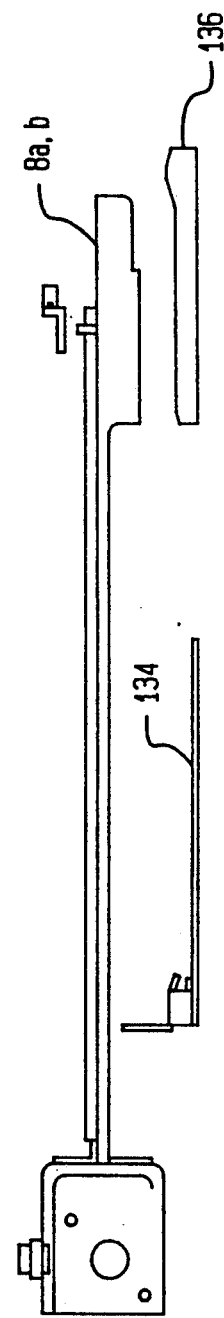

FIG. 9 shows the relative positions of draw bar 134, clamp arms 8a, b and riser 136, when assembled.

The operation of the device will now be described. Initially, when the device is first turned on, and a film cassette has not yet been inserted, carriage 4 is caused to move to a rearward position, due to simultaneous rotation of belts 36 and 38, until sensor 122 provides a signal indicating that carriage 4 is in its rearmost position, and thereafter only belt 36 is caused to rotate (i.e., clutch brake 28 is caused to be in its brake mode), so as to drive clamp arms 8a, b to the HOME position wherein sensor 126 will then indicate that motor 22 should be deenergized.

Next, belts 36 and 38 are simultaneously driven to move carriage 4 forward to the LOAD position wherein slot 20 of clamp arm 8a will engage pin 154 of frame 2 to cause arm 8a to be held in the "wide-open" position and lever 142 of nut clamp means 21 will engage a bevelled portion 160 of frame 2 (shown in FIG. 8) to unclamp following nut 19 so as to allow rotational movement of nut 19 with respect to clamp arm 8a. Next only belt 36 is rotated so as to cause clamp arm 8b to move away from clamp arm 8a to a full open position. Next, only belt 36 is rotated so as to cause clamp arm 8b to be driven towards clamp arm 8a and the pulses used to drive motor 22 are counted so as to determine the amount of movement of clamp arm 8b providing an indication of cassette width. If it is determined by the movement of clamp arm 8b that a film cassette is not present, both belts are driven to cause carriage 4 to return to the HOME position and a "C" is caused to be shown in display 76 on control panel 72, indicating that a film cassette is required to be inserted.

If it is determined by the movement of clamp arm 8b that a film cassette is present, both belts are driven to cause carriage 4 to travel rearward and the pulses used to drive motor 22 are counted until magnet 156 passes over sensor 158 so as to determine the amount of rearward movement of drawbar 134 providing an indication of cassette length. Carriage 4 continues rearward until reaching the HOME position.

Next, if no cassette was present, the operator presses a "LOAD" button on control panel 72, causing carriage 4 to be moved forward into the LOAD position and the operator inserts a film cassette into opening 73. The operator then hits the LOAD button again. In response thereto, belt 36 is caused to rotate, causing lead-screw 20 to rotate and clamp arm 8b to move towards clamp arm 8a, and thereby come to an abrupt halt when the inserted film cassette is grasped. Due to the force of clamp arm 8b being driven against the film cassette, upon tightening, the braking action caused by clutchbrake 28 against belt 38 is temporarily overridden. This causes carriage 4 to move slightly rearward, which in turn causes the clamp lever 142 of nut clamping mechanism 21 to move away from bevel 160, thereby allowing clamp spring 144 to again urge clamp plate 138 against following nut 19, so as to prevent rotation of following nut 19 with respect to clamp arm 8a. Furthermore, the slight rearward movement of carriage 4 causes flag 96 to break contact with sensor 90, which sensor then provides a signal which is used to cause clutchbrake mechanism 28 to return to its clutch mode. Thereafter, both of belts 36 and 38 are driven in unison, causing front to back movement of clamp arms 8a, b and, upon selective changing of clutchbrake 28 to the brake mode, selective rotation of motor 22 will cause clamp arms 8a, b to move left and right so as to thereby provide full x,y translational movement of the grasped film cassette.

The width (y-axis direction) of the inserted film cassette is determined by counting the pulses supplied to motor 22 during the time period between when sensor 90 senses that clamp arm 8b is first driven towards the film cassette and when sensor 92 senses that carriage 4 has moved slightly towards the rear. The length (or x-axis direction) of the inserted film cassette is measured by counting motor pulses during the time period between when sensor 92 senses that carriage 4 is first moved towards the rear and when magnet 156 mounted in the lower center portion of draw bar 134 passes over Hall-effect sensor 158 mounted in the middle bottom portion of frame 2. The information concerning the amount of clock pulses used to drive the motor during the above-noted time periods is sent to the spot film device microprocessor (not shown) which uses that information in order to determine the length and width of the inserted film cassette, which dimensions are used thereafter in order to control proper positioning of the film cassette in differently selected operator sequences.

Thus, there has been shown and described a novel dual axis translating mechanism which can rapidly grasp and position an object having a variable size at any desired position along first and second axes in a simple, efficient and reliable manner. While present market devices use multiple motors or motor/spring combinations for the sole purpose of cassette grasping and sizing, the present invention requires no additional motor for these functions, using only the single motor used for x, y translation. This results in lower manufacturing costs, improved reliability, as well as lower servicing costs, reduced size and weight, etc. Many changes, modifications, variations and other uses and applications of the subject invention will, however, become apparent to those skilled in the art after considering this specification and its accompanying drawings, which disclose preferred embodiments thereof. For example, clutch/brake assembly 28 and coupling 26 could be replaced by a functional equivalent, such as a second independently controllable stepper motor which can be operated synchronously with motor 22 for obtaining the clutch (or drive) mode and energized so as to act as a brake for obtaining the brake mode. Of course, it should also be recognized that other types of motors could be used, such as a servo-motor. Furthermore, following nut 19 could be replaced by a bushing and clamp mechanism 21 could be eliminated. In this alternative, a constant force reel spring would be located on arm 8b and connected to arm 8a via a cable, so as to constantly urge arm 8b towards and follow the y-axis movement of arm 8a. Furtheremore, for determining the movement of clamp arm 8b and carriage 4 when calculating the size of the inserted film cassette, instead of counting the number of pulses used to drive motor 22, which in the preferred embodiment using a stepping motor results in a predefined x, y movement, in an alternative embodiment, just the time period during which motor 22 is energized could be monitored to provide this information. All such changes, modifications, variations and other uses and applications which do not depart from the spirit and scope of the invention are deemed to be covered by the invention which is limited only by the claims which follow.

What I claim is:

1. A mechanism for selective grasping and translation of an object to a position defined by first and second axes, comprising:

a frame;

a carriage mounted on said frame via a first guide means for movement of said carriage with respect to said frame along a first axis;

a holder for selectively grasping said object;

intermediate mounting means coupled with said holder and said carriage for mounting said holder on said carriage via a second guide means for movement of said holder with respect to said carriage along a second axis which is different from said first axis;

a motor means for selectively driving a first belt;

a drive/brake assembly coupled to said motor means for selectively driving a second belt which, in a drive mode of said assembly is driven synchronously with said first belt and, which in a brake mode of said assembly is held non-driven while said first belt is being driven; and said first belt being coupled to the second guide means of said intermediate mounting means for selectively moving said object holder in a direction parallel to said second axis in response to movement of said first belt and said second belt being coupled with said carriage for selectively moving said carriage in a direction parallel to said first axis in response to movement of said second belt; wherein, said object holder comprises first and second clamp arms;

the second guide means of said intermediate mounting means comprises a lead-screw having an end coupled to receive rotational movement from said first belt, and carries first and second nuts thereon, which nuts are coupled to said first and second clamp arms, respectively; and said first nut being threaded onto the lead screw and non-rotatably attached to the first clamp arm for preventing rotation of the first nut with respect to the first clamp arm, and said second nut being rotatably attached to the second clamp arm for permitting the second nut to at least selectively rotate with respect to the second clamp arm, whereby the spacing between said clamp arms is selectively controlled to cause said clamp arms to grasp and thereafter translate said object along said second axis.

2. An apparatus for grasping and translating an object to positions defined by first and second axes, comprising:

a frame;

a carriage mounted on said carriage for movement relative to said cartridge along said second axis, said holder having a pair of adjustably spaced apart clamp arms for grasping objects of variable size;

a motor;

a first translation mechanism coupled to said motor and said holder for selectively moving said holder along said second axis in response to actuation of said motor;

a second translation mechanism coupled to said motor and said carriage for selectively moving said carriage along said first axis in response to actuation of said motor; and a control mechanism coupled between said holder and said first translation mechanism said holder for selectively controlling the spacing between said arms for causing said arms to grasp and thereafter translate said object along said second axis.

3. The apparatus of claim 2, wherein said first translation mechanism comprises a first pulley mechanism having a first belt, means for transmitting drive force from said motor to said first pulley mechanism, and means for transmitting motion of said first belt to said holder to move said holder along said second axis.

4. The apparatus of claim 3, wherein said means for transmitting motion of said first belt comprises a drive pulley mounted for rotation in response to movement of said first belt and a lead screw secured to said drive pulley for rotation in unison therewith, and said holder includes means forming a threaded opening coupled to said lead screw, whereby rotation of said lead screw causes said holder to move along the length of said lead screw.

5. The apparatus of claim 4, wherein said means forming a threaded opening comprises a first follower non-rotatably secured to a first one of said clamp arms.

6. The apparatus of claim 5, wherein said control mechanism comprises means coupled between a second one of said clamp arms and at least one of said frame and said holder for selectively preventing movement of said second one of said clamp arms as rotation of said lead screw causes said first clamp arm to move relative to said second clamp arm.

7. The apparatus of claim 5, wherein said means forming a threaded opening further comprises a second follower selectively fixably secured to a second one of said clamp arms so as to selectively cause positioning of said second clamp arm along said lead screw in response to rotation of said lead screw.

8. The apparatus of claim 7, wherein said control mechanism comprises means coupled between said second clamp arm and at least one of said frame and said holder for selectively preventing movement of said second clamp arm along said lead screw as rotation of said lead screw causes said first clamp arm to move relative to said second clamp arm.

9. The apparatus of claim 8, wherein said means for selectively preventing movement of said second clamp arm comprises means for selectively allowing said second follower to rotate relative to said second clamp arm.

10. The apparatus of claim 9, wherein said means for selectively allowing said second follower to rotate relative to said second clamp arm comprises a releasable mechanism for clamping said second follower to said second clamp arm.

11. The apparatus of claim 10, wherein said releasable mechanism for clamping includes:

a clamp plate coupled to said holder for clamping said second follower against said second arm so as to substantially prevent rotational movement therebetween;

a lever pivotally secured to said second arm;

a wire connecting one end of said lever to said clamp plate;

a spring secured to one end to said second arm and at its other end to the other end of said lever, whereby said spring biases said lever to a position in which said wire is held taught and said clamp plate holds said second follower against said second arm; and means for selectively pivoting said lever so that said clamp plate releases said second follower.

12. The apparatus of claim 11, wherein said means for selectively preventing movement of said second arm further comprises pin-and-slot means on said second arm and said frame, respectively, for retaining said second arm stationary with respect to said frame when said holder moves to a position in which said pin engages said slot.

13. The apparatus of claim 12, wherein said means for selectively pivoting said lever comprises a bevelled portion of said frame which engages said lever when said holder moves to said position in which said pin engages said slot.

14. The apparatus of claim 8, wherein said means for selectively preventing movement of said second arm further comprises pin-and-slot means on said second arm and said frame, respectively, for retaining said second arm stationary with respect to said frame when said holder moves to a position in which said pin engages said slot.

15. The apparatus of claim 3, wherein said second translation mechanism includes a second pulley mechanism including a second belt, a connector securing said carriage to said second belt for travel in unison therewith, and means for selectively transmitting drive force from said motor to said second pulley mechanism.

16. The apparatus of claim 15, wherein said means for selectively transmitting drive force comprises a clutch-brake and a pair of drive shafts connecting said motor to said clutch-brake and connecting said clutch brake to said second pulley mechanism, respectively.

17. The apparatus of claim 16, wherein said means for transmitting motion of said first belt includes a drive pulley mounted for rotation in response to movement of said first belt and a lead screw secured to said drive pulley for rotation in unison therewith, and said holder has means forming a threaded opening coupled to said lead screw, whereby rotation of said lead screw causes said holder to move along the length of said lead screw.

18. The apparatus of claim 17, wherein said means forming a threaded opening comprises a first follower non-rotatably secured to a first one of said clamp arms and a second follower rotatably secured to a second one of said clamp arms thereby permitting a static positioning of said second clamp arm along said lead screw irrespective of the rotation of said lead screw, and said control mechanism comprises means coupled between said second clamp arm and at least one of said frame and said holder for selectively preventing movement of said second clamp arm as rotation of said lead screw causes said first clamp arm to move relative to said second clamp arm.

19. The apparatus of claim 18, wherein said control mechanism comprises means for selectively preventing movement of said second clamp arm along said lead screw as rotation of said lead screw causes said first clamp arm to move relative to said second clamp arm, including a releasable mechanism for selectively clamping said second follower to said second clamp arm, wherein said releasable mechanism includes:

a clamp plate coupled to said holder for clamping said second follower against said second arm so as to substantially prevent rotational movement therebetween;

a lever pivotally secured to said second arm;

a wire connecting one end of said lever to said clamp plate;

a spring secured at one end to said second arm and at its other end to the other end of said lever, whereby said spring biases said lever to a position in which said wire is held taught and said clamp plate holds said second follower against said second arm; and means for selectively pivoting said lever so that said clamp plate releases said second follower.

20. The apparatus of claim 2, wherein said motor is also coupled to said control mechanism for actuating said control mechanism.

21. The apparatus of claim 20, further including sensor means coupled to said motor for determining the amount of movement of one of said clamp arms along said second axis from a full open position to a position at which said one of said clamp arms engages said object.

22. The apparatus of claim 21, wherein said sensor means comprises:

a pulse counter which provides a signal which is a measure of drive pulses applied to said motor during movement of one of said clamp arms along said second axis from said full open position to said position at which said one of said clamp arms engages said object;

a pair of sensors coupled to said frame for providing signals determinative of when said one of said clamp arms begins and ends its movement from said full open position to the position at which it engages said object; and a microprocessor which determines the width of said object in response to signals provided from said sensors and said pulse counter.

23. The apparatus of claim 2, further comprising means for determining the length of said object grasped by said clamp arm, comprising:

sensor means coupled between said frame and said holder for determining the amount of movement of a leading edge of said object along said first axis from a predetermined front position on said frame to a predetermined location rearward on said frame.

24. The apparatus of claim 23, wherein said leading edge movement determining means comprises a magnet and hall-effect sensor, one of which is mounted on said frame and the other of which is mounted on said holder.

25. The apparatus of claim 23, wherein said leading edge movement determining means comprises a pulse counter which provides a signal which is a measure of pulses applied to drive said motor during movement of said object from said predetermined front position to said predetermined rearward location on said frame; and said length determining means further comprises a pair of sensors for providing signals determinative of when said object begins and ends its movement from said predetermined front position to said predetermined rearward location on said frame, and a microprocessor which determines the length of said object in response to signals provided from said sensors and said pulse counter.

26. The apparatus of claim 25, wherein one of said sensors comprises a hall-effect sensor mounted on said frame which senses movement of a magnet mounted on a draw bar of said holder, which draw bar engages said leading edge of said object.

27. An apparatus for grasping and translating an object to positions defined by first and second axes, comprising:
- a frame;
- a carriage mounted on said frame for movement along said first axis;
- a holder mounted on said carriage for movement relative to said carriage along said second axis, said holder having a pair of adjustably spaced apart first and second clamp arms for grasping objects of variable size;
- a first translation mechanism coupled to said holder for selectively moving said holder along said second axis;
- a second translation mechanism coupled to said carriage for selectively moving said carriage along said first axis; and
- a control mechanism coupled to said holder for selectively controlling the spacing between said clamp arms for causing said arms to grasp and thereafter translate said object along said second axis, said control mechanism including a lead screw coupled to and rotatably driven by said first translation mechanism and extending in the direction of said second axis, said holder including means forming first and second threaded openings which couple said first and second clamp arms, respectively, to said lead screw, and whereby rotation of said lead screw causes said holder and clamp arms to move along the length of said lead screw.

28. The apparatus of claim 27, wherein said means forming a threaded opening comprises a first follower non-rotatably secured to a first one of said clamp arms and a second follower rotatably secured to a second one of said clamp arms thereby permitting a stationary positioning of said second clamp arm irrespective of the rotation of said lead screw, and thereby causing said first clamp arm to move relative to said second clamp arm.

29. The apparatus of claim 28, wherein said first translation mechanism comprises a motor, a first pulley mechanism having a first belt, means coupled between said motor and said first pulley mechanism for transmitting drive force from said motor to said first pulley mechanism, and means coupled between said first belt and said lead screw for transmitting motion of said first belt to said lead screw to move said holder along said second axis.

30. In an apparatus for grasping and translating an object to positions defined by first and second axes, including a frame, a carriage mounted on said frame for movement along said first axis, a holder mounted on said carriage for holding the object, a motor, a first translation mechanism coupled between said motor an said carriage for selectively moving said carriage along said first axis in response to actuation of said motor, and a second translation mechanism coupled between said motor and said holder for selectively moving said holder along said second axis in response to actuation of said motor, wherein the improvement comprises:
- said holder includes a pair of adjustably spaced-apart, movable clamp arms coupled to said motor via said second translation mechanism for selectively grasping and thereafter translating along said second axis objects of variable size.

31. The apparatus of claim 30, further comprising a control mechanism coupled to said holder for selectively opening and closing said clamp arms in response to actuation of said motor, said motor being coupled to operate all three of said first translation mechanism, said second translation mechanism, and said grasping mechanism.

32. The apparatus of claim 30, further comprising a lead screw rotatably driven by said first translation mechanism and extending in the direction of said second axis, said holder including means forming a threaded opening coupled to said lead screw, and whereby rotation of said lead screw causes said holder to move along the length of said lead screw.

33. The apparatus of claim 32, wherein said means forming a threaded opening comprises a first follower non-rotatably secured to a first one of said clamp arms and a second follower rotatably secured to a second one of said clamp arms, thereby permitting a stationary positioning of said second clamp arm along said lead screw irrespective of the rotation of said lead screw.

* * * * *